United States Patent
Ataullakhanov et al.

(10) Patent No.: US 9,938,563 B2
(45) Date of Patent: Apr. 10, 2018

(54) METHOD FOR DETERMINING THE SPATIOTEMPORAL DISTRIBUTION OF ACTIVITY OF A PROTEOLYTIC ENZYME IN A HETEROGENEOUS SYSTEM (VARIATIONS), A DEVICE FOR REALIZING SAME AND A METHOD FOR DIAGNOSING THE DEFECTS IN THE HEMOSTATIC SYSTEM ON THE BASIS OF A CHANGE IN THE SPATIOTEMPORAL DISTRIBUTION OF ACTIVITY OF A PROTEOLYTIC ENZYME IN A HETEROGENEOUS SYSTEM

(75) Inventors: Fazoil Inoyatovich Ataullakhanov, Moscow (RU); Nataljya Mikhajlovna Dashkevich, Pyschino (RU); Mikhail Vladimirovich Ovanesov, Zelenograd (RU); Vasilii Ivanovich Sarbash, Moscow (RU); Mikhail Aleksandrovich Panteleev, Mytishchi (RU); Sergey Sergeevich Karamzin, Moscow (RU); Andrey Yurjevich Kondratovich, Moscow (RU)

(73) Assignee: OBSCHESTVO S OGRANICHENNOY OTVETSTVENNOSTYU GEMATOLOGICHESKAYA KORPORATSIYA, Moscow (RU)

( * ) Notice: Subject to any disclaimer, the term of this patent is extended or adjusted under 35 U.S.C. 154(b) by 104 days.

(21) Appl. No.: 14/234,909

(22) PCT Filed: Jul. 16, 2012

(86) PCT No.: PCT/RU2012/000570
§ 371 (c)(1),
(2), (4) Date: Apr. 11, 2014

(87) PCT Pub. No.: WO2013/015717
PCT Pub. Date: Jan. 31, 2013

(65) Prior Publication Data
US 2014/0227726 A1    Aug. 14, 2014

(30) Foreign Application Priority Data
Jul. 26, 2011    (RU) ................................ 2011131293

(51) Int. Cl.
*C12Q 1/56*    (2006.01)
*C12Q 1/37*    (2006.01)
*G01N 21/64*    (2006.01)

(52) U.S. Cl.
CPC ................. *C12Q 1/56* (2013.01); *C12Q 1/37* (2013.01); *G01N 21/6408* (2013.01);
(Continued)

(58) Field of Classification Search
None
See application file for complete search history.

(56) References Cited

U.S. PATENT DOCUMENTS

| 5,059,525 A | 10/1991 | Bartl |
| 5,339,830 A | 8/1994 | Blake |

FOREIGN PATENT DOCUMENTS

| WO | 9310261 | 5/1993 |
| WO | 2009098313 | 8/2009 |

OTHER PUBLICATIONS

Ataullakhanov ("Mathematical Modeling and Computer Simulation in Blood Coagulation", Pathophysiol Haemost Thromb 2005;34:60-70).*

(Continued)

*Primary Examiner* — Michael Borin
(74) *Attorney, Agent, or Firm* — Volpe and Koenig, P.C.

(57) ABSTRACT

The invention relates to the field of biotechnology. The method for determining the spatial and temporal distribution
(Continued)

of the activity of a proteolytic enzyme in an in vitro heterogeneous system, such as blood or blood plasma, involves the introduction of a luminescent, fluorogenic or chromogenic substrate into a sample with the subsequent release of a detectable tag as the proteolytic enzyme cleaves the substrate, and the recording of the optical characteristics of the sample, which makes it possible to assess the spatial and temporal distribution of the activity of the enzyme. The device for the implementation of the above method comprises an in vitro system, a means for illuminating the sample, a recording means and a control means. A method for diagnosing homeostatic imbalances according to a change in the spatial and temporal distribution of the activity of a proteolytic enzyme in a blood sample is also proposed.

13 Claims, 5 Drawing Sheets

(52) U.S. Cl.
CPC . *G01N 21/6456* (2013.01); *G01N 2021/6439* (2013.01); *G01N 2333/95* (2013.01); *G01N 2333/974* (2013.01)

(56) References Cited

OTHER PUBLICATIONS

Legawiec et al. J. Phys. Chem. A 1997, 101, 8063-8069.*
Cherniha et al. In "Mathematical Modeling of Biological Systems, Volume I", Deutsch et al. Editors, Springer, 2007, pp. 281-288.*
Ataullakhanov et al. Biochimica et Biophysica Acta 1425, 1998, 453-468.*
Kondratovich et al., 2002, "Spatiotemporal dynamics of contact activation factors of blood coagulation," Biochim Biophys Acta 1569: 86-104.
Fadeeva et al., 2010, "Thromboplastin immobilized on polystyrene surface exhibits kinetic characteristics close to those for native protein and activates in vitro blood coagulation similarly to thromboplastin on fibroblasts," Biochemistry 75(6): 734-743.
International Search Report and Written Opinion issued in International Patent Application No. PCT/RU2012/000570 dated Dec. 20, 2012, and the ISR English Translation.

* cited by examiner

METHOD FOR DETERMINING THE SPATIOTEMPORAL DISTRIBUTION OF ACTIVITY OF A PROTEOLYTIC ENZYME IN A HETEROGENEOUS SYSTEM (VARIATIONS), A DEVICE FOR REALIZING SAME AND A METHOD FOR DIAGNOSING THE DEFECTS IN THE HEMOSTATIC SYSTEM ON THE BASIS OF A CHANGE IN THE SPATIOTEMPORAL DISTRIBUTION OF ACTIVITY OF A PROTEOLYTIC ENZYME IN A HETEROGENEOUS SYSTEM

This application is a 35 U.S.C. § 371 national phase application of PCT/RU2012/000570, which was filed Jul. 16, 2012, and claims the benefit of Russian patent application No. 2011131293, filed Jul. 26, 2011, both of which are incorporated herein by reference as if fully set forth.

TECHNICAL FIELD

The present invention relates to medicine and biology and can be used, in particular, for diagnostic and research purposes to determine coagulation characteristics of blood and its components, as well as in biotechnology, pharmacology, and in fundamental biological research.

BACKGROUND ART

A big problem currently exists in studying the dynamics of complex biological systems and processes occurring in them, where there is spatial heterogeneity. Such processes include, in particular, blood coagulation, complement, apoptosis, digestion, fibrinolysis, in which proteolytic enzymes (proteinases) play a key role.

Concentration of proteolytic enzymes can be measured if this value is unchanging in time and is the same at all points of the sample being analyzed with the use of a specific fluorogenic substrate or a chromogenic substrate. Currently, methods measuring changes in concentration over time are used in fundamental research and in diagnostics of functional failures of the corresponding biological systems. To determine blood coagulation disorders, a test of thrombin generation in plasma is now used, which was disclosed in the basic paper by Hemker H C, Wielders S., Kessels H., Beguin S., *Continuous registration of thrombin generation in plasma, its use for the determination of the thrombin potential*, J Thromb Haemost. 1993, Oct. 18, 70 (4):617-24. The test has demonstrated many advantages over traditional coagulation tests, but it is spatially uniform, i.e. a homogeneous environment is studied. This doesn't correspond to the situation in the organism described below.

Figure 1:
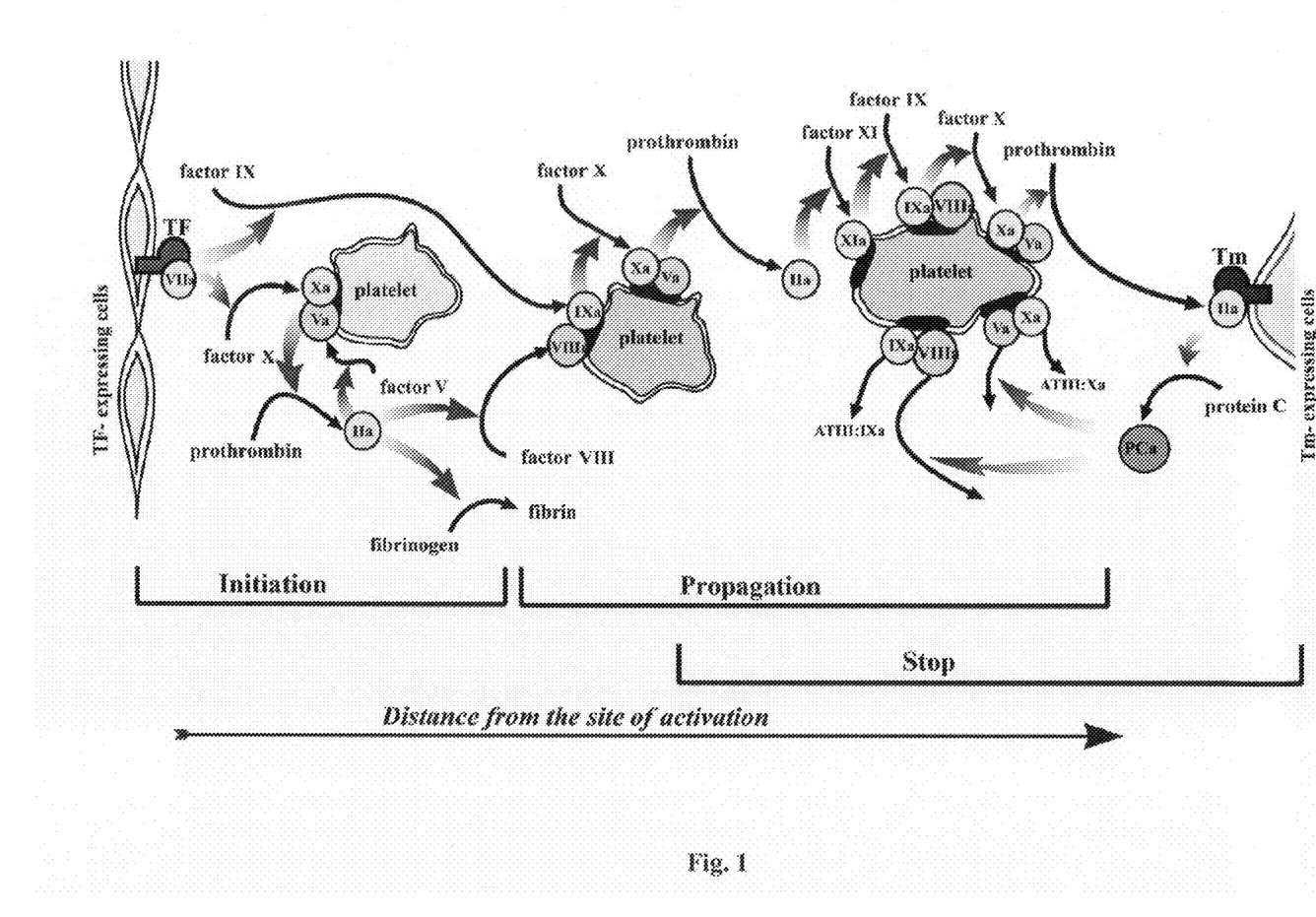
FIG. 1 depicts schematically the spatial concept of blood coagulation regulation.

FIG. 1 schematically represents the spatial concept of regulation of blood coagulation. Coagulation is activated by cells expressing a transmembrane protein—tissue factor, a nonenzymatic co-factor being a coagulation factor (left), —and propagates deep into the plasma. The generation of thrombin is regulated by activated factor X (factor Xa, serine proteinase), a limiting component of prothrombinase. The coagulation near the activator (the initiation phase) is determined solely by production of factor Xa by extrinsic tenase—a complex of tissue factor and serine proteinase of factor VIIa. However, factor Xa is inhibited rapidly and cannot diffuse far away from the activator. Therefore, during the clot propagation phase it is formed by intrinsic tenase. The limiting component of the intrinsic tenase, clotting factor IXa, is produced by extrinsic tenase. In contrast to factor Xa it is inhibited slowly and therefore diffuses far away. Following further increase of the clot, additional factor IXa is produced by factor XIa, which in turn is produced by thrombin within a positive feedback loop. The clot formation stops due to the action of thrombomodulin: a negative feedback loop activates protein C, which stops propagation of thrombin by destruction of factors Va and VIIIa (see Panteleev M. A., Ovanesov M. V., Kireev D. A., Shibeko A. M, Sinauridze E. I., Ananyeva N. M., Butylin A. A., Saenko E. L., and Ataullakhanov F. I., *Spatial Propagation and Localization of Blood Coagulation Are Regulated by Intrinsic and Protein C Pathways, Respectively*, Biophys J. 2006 Mar. 1; 90(5):1489-500). Despite the fact that some details of this concept can be corrected, the key role of diffusion processes and spatial heterogeneity in clotting is undisputed (Hoffman M., Monroe D M 3$^{rd}$, *A cell based model of hemostasis*, Thromb Haemost. 2001 June; 85(6):958-65).

Thrombin is the key enzyme of the blood coagulation system. It catalyzes the main reaction—the conversion of fibrinogen into fibrin. In addition, thrombin activates coagulation factors V, VIII, VII, XI, XIII, protein C, platelets, thrombin-activated fibrinolysis inhibitor. In coagulation, the volume of thrombin produced is 10-100 times bigger than the one of the other proteinases, which facilitates its detection.

In the thrombin-catalyzed reaction, fibrinogen is converted into fibrin, which polymerizes and thus jellifies blood plasma.

Studies of blood coagulation are of great practical interest because they do not only allow certain diseases to be diagnosed, but also make it possible to assess the activity of drugs affecting blood coagulation parameters.

Appearance of chromogenic and then fluorogenic substrates accelerated the coagulation studies. Such synthetic substrate is a molecule that is recognized and cut by proteolytic enzyme. Cutting leads to cleavage from the substrate of a signaling molecule also referred to as "mark". The mark either changes the optical density of the solution (chromogenic or coloring substrate), or can fluoresce when illuminated (fluorogenic substrate), or can spontaneously emit light without external excitation (chemiluminescent mark). Substrates for thrombin can be added directly into plasma, and the signal (optical density or light intensity) appearing in coagulation can be recorded. The rate of increase of the signal is proportional to concentration of thrombin. Thrombin dependence on time is obtained from the experimental relation between signal and time by simple differentiation and calculation of thrombin concentration based on the substrate cleavage rate using the calibration curve obtained by adding to a buffer or plasma under analysis of known concentrations of thrombin or another calibrator (e.g. complex of thrombin and alpha2-macroglobulin).

Various methods and devices are known from the background art for determining blood coagulation parameters in-vitro. However, all known methods and devices are usually designed to work within homogeneous systems, where a sample of blood or plasma is uniformly mixed with an activator, which substantially distinguishes these systems from the system in-vivo being a complex heterogeneous environment.

In a well-known model, the in-vitro systems' conditions of the coagulation process are fundamentally different from the conditions in which the clot is formed in a living organism. It is known that in the circulatory system of humans and animals a clot is formed not in the entire volume of blood plasma, but strictly locally, i.e. in a small area near the damaged blood vessel wall. Clotting in the body is not uniform. Formation of a clot occurs in space. It is induced by extrinsic tenase on a damaged vessel wall, propagates with participation of prothrombinase on the activated platelets in the bulk of plasma, and is inhibited by reactions involving thrombomodulin on healthy endothelium. In this case coagulation factors are naturally distributed in a small volume of plasma, and a clot forms therein. This reflects the basic defense mechanism of the hemostatic system: maintenance of integrity of the bloodstream through formation of a blood clot at the site of injury. These processes cannot be adequately studied using the methods carried out in a homogeneous medium.

Thus, there is currently a problem of experimental modeling of blood coagulation in-vitro, as it is desirable to more fully simulate the spatial situation in which a blood clot coagulates directly in a blood vessel. The problem exists both for fundamental studies of thrombosis and hemostasis, and for application-specific diagnostic and pharmacological tasks.

The problem of determining the changes of the proteolytic enzyme concentration in time and space, i.e. at different points within the volume of the test sample, has not been solved yet.

Recently, devices have been used which allow taking into account the spatial heterogeneity and diffusion of coagulation factors. In such devices, coagulation occurs in a cuvette containing recalcified plasma. The activator is a surface with immobilized clotting activator, e.g. tissue factor. Coagulation begins upon contact of the activator with the plasma and then propagates deeper into the plasma; it can be observed by light scattering from the growing clot.

From the background art, we know a device for investigation of coagulation characteristics of blood and its components (patent RU 2395812, cl. G01N33/49, published on 27, Jul. 2010) comprising a thermostatically controlled chamber which accommodates a cuvette with a test plasma sample and a coagulation activator, such as thromboplastin (coagulation tissue factor) applied on the insert put into the cuvette, LEDs for lightening the cuvette content and a clot forming near the activator, a digital camera recording the growing clot, and a computer for processing the obtained data.

This device allows implementing a method which involves recording only the process of formation of a fibrin clot being the final product of the coagulation system.

We also know a method and an apparatus for monitoring the spatial fibrin clot formation (International application PCT/CH2007/000543, cl. G01N33/49, published on 7, May 2009, publication number WO 2009/055940).

The apparatus comprises a cuvette used for photometric analysis, comprising a chamber, an insert and an activator, a thermostat wherein the said cuvette is placed. The coagulation activator is located on the bottom edge of the insert. The coagulation activator is a physiological activator, such as tissue factor, or a non-physiological activator, such as glass. The cuvette is made of light-transmitting polystyrene.

The device allows in-vitro monitoring of formation and/or lysis of a fibrin clot and comprises the following steps:

placing in a cuvette one or more plasma samples depending on the number of wells, and inserting into the cuvette an insert with an activator and bringing plasma into contact with a coagulation activator (in case of clot formation), and recording the growth of the fibrin clot as a function of time and distance, or placing in the cuvette one or more plasma samples containing one or more fibrin clots, bringing plasma into contact with a fibrinolysis activator (in case of clot lysis), and recording the lysis of the fibrin clot as a function of time and distance.

The principal advantage of the method and apparatus for monitoring spatial fibrin clot formation is that only a small volume of plasma is needed. With as small amount as 20 μl (instead of 300 up to 1500 μl, i.e. 75-fold less than in the other similar system reported previously, and 5-fold less than the minimal plasma amount required for standard clotting assays), reliable high resolution results can be produced. This apparatus allows implementing a method which involves recording only the formation process of a fibrin clot being the final product of the coagulation system.

The disadvantage of the abovementioned device and method is the formation of gas bubbles in the cuvette within the registration area when the test samples are heated, which distorts the light scattering signal from the fibrin clot.

Light sources having only one wavelength, such as red light, prevent the study of spatiotemporal distribution of fluorescent substances.

Moreover, the device and method described above do not provide the possibility to record the process of formation and spatial distribution of separate clotting factors, such as IIa, Xa, VIIa, XIa, which regulate the process of spatial fibrin clot growth.

Most closely related to the present method and device are the apparatus and method disclosed in article by Kondratovich A. Y., Pohilko A. V. and Ataullahanov F. I., *Spatiotemporal Dynamics of Contact Activation Factors of Blood Coagulation*, Biochim Biophys Acta. 2002 Jan. 15; 1569 (1-3):86-104).

To carry out the abovementioned method, platelet-poor plasma is used. Distributions of factor XIa and kallikrein of the studied plasma sample are determined by recording the indigo emission of 7-amino-4-methyl-coumarin (AMC), product of cleavage of fluorogenic substrates specific to these factors.

Prior to the measurements, a substrate was added to each test plasma sample, and the sample was stirred at 37 degrees C.; pH of the medium was maintained at 7.4 at this temperature.

Figure 2:
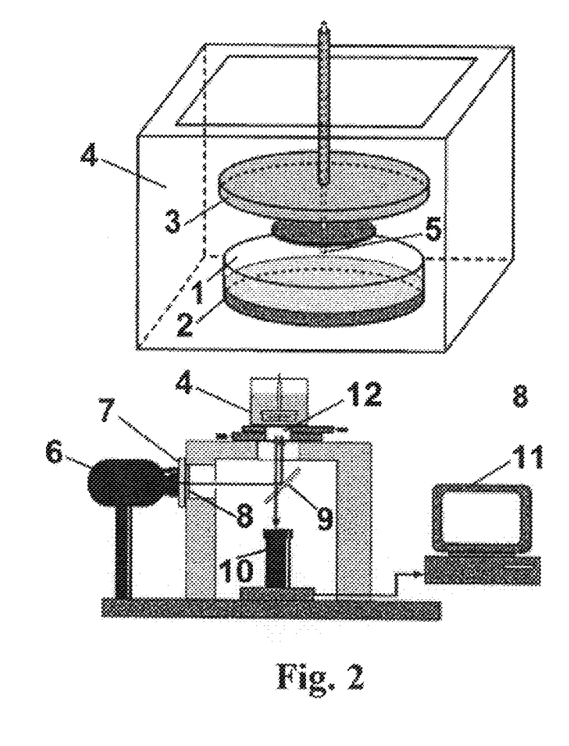
FIG. 2 is a schematic diagram of a known device for determining spatial dynamics of the coagulation factors.

FIG. 2 shows schematically a device used to implement the method. The device comprises a polystyrene dish 1 containing the studied blood plasma sample 2. The substrate is added to plasma 2. The tip 5 of the glass capillary was used as a coagulation activator. The device also contains: light source 6—a mercury lamp, thermostat 7, glass filter 8, semitransparent mirror 9, digital camera 10, fluorescing plastic label 12; the device is plugged to computer 11.

Activation of clotting factors was studied in a two-dimensional (flat) medium, that is, in a thin layer of unstirred plasma. Dish 1 was transferred to thermostat 7 at 37 degrees C., and the activator was quickly lowered so that capillary end 5 would be submerged into the plasma.

The coagulation factor activated by contact with glass cleaved the substrate, giving rise to formation of AMC. Fluorescence of AMC was recorded as follows. The plasma sample was lightened by light from light source 6 reflected from semitransparent mirror 9. Filters 8 blocked the visible portion of the light source spectrum. AMC fluorescence was recorded by digital camera 10 mounted behind the semi-transparent mirror. The recorded field of view measured 9.0×6.5 mm. Blue channel of the RGB output signal of the camera spanned the entire range of AMC fluorescence. The image data was continuously transferred to computer 11, displayed on its monitor and saved at specified intervals. Piece of fluorescing plastic 12 was fixed beneath thermostat 7 so that its image was always in the field of view of the camera; this was used for calibration and for taking into account the light variation.

Figure 3:
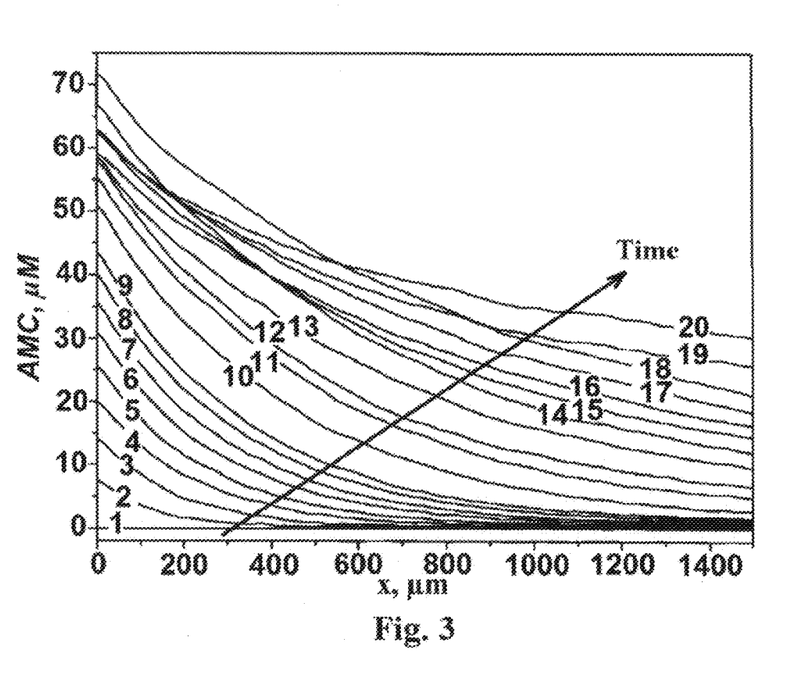
FIG. 3 shows typical dependences of AMC concentration on distance and time obtained in studies of spatiotemporal distribution of clotting factor XIa; coagulation activator is located at the origin of coordinates.

In analysis of the images, a radial line beginning in the activator's center was selected. The spatiotemporal distribution of AMC concentration along the line was determined by specific software (FIG. 3), and the spatiotemporal distribution of clotting factor concentration was recovered on its basis.

Disadvantages of this method include the ability of measuring only contact activation factors (particularly, factors XIa, XIIa, kallikrein) with poor ability of differentiating between contributions of these factors into signal and without the possibility of measuring the spatial dynamics of coagulation process, i.e. formation of a fibrin clot.

Disadvantages of the apparatus include: inconvenience of the used dish for high efficiency studies; use of unstable illumination with a mercury lamp, which doesn't allow taking precise measurements; formation of gas bubbles in the area where the process is recorded while the test samples are heated, distorting the fluorescence signal.

The method does not allow modeling in-vitro systems that are similar in their physiological properties to in-vivo systems, and does not allow a more accurate diagnosis of disorders in the blood coagulation system.

Moreover, the above method doesn't allow adequate investigation of the spatial kinetics of coagulation factors, first of all thrombin, during the process of fibrin clot growth, and does not provide the opportunity to evaluate the role of coagulation factor in the different phases of the blood coagulation process in a heterogeneous system.

Thus there is a clear need to improve existing methods and devices for better determination of blood and blood components' coagulation properties.

SUMMARY OF THE INVENTION

The object of the present invention is the investigation of spatial dynamics of coagulation factors in the process of fibrin clot growth and assessment of the role of coagulation factors in different phases of the blood coagulation process in a heterogeneous system, which can be used to diagnose some diseases and to evaluate the activity of drugs influencing blood coagulation parameters.

The technical result which can be obtained through realization of the claimed solution is the enhancement of the method sensitivity to disorders in plasma and platelet parts of the blood coagulation.

The object is accomplished by providing a method for determining the spatiotemporal distribution of the proteolytic enzyme activity in a heterogeneous system, comprising the following steps:

providing an in-vitro system that includes a sample of a test medium, wherein the test medium is selected from the group consisting of blood plasma, whole blood, water, lymph, colloidal solution, crystalloid solution and gel, and a proteolytic enzyme or its zymogen, wherein the proteolytic enzyme or its zymogen is distributed in the sample of the test medium;

combining (immersing or contacting) a fluorogenic substrate with the in-vitro system, wherein the fluorogenic substrate is cleaved by the proteolytic enzyme, and a fluorescent mark is released upon cleavage of the fluorogenic substrate;

illuminating the sample of the test medium to excite a fluorescence signal of the fluorescent mark;

recording the spatial distribution of the fluorescence signal of the fluorescent mark in the sample of the test medium, and obtaining a set of distributions of the fluorescence signal; and calculating the spatiotemporal distribution of the proteolytic enzyme activity by using the set of spatial distributions of the fluorescence signal and solving the inverse "reaction-diffusion-convection" problem, wherein the step of calculating includes correcting the spatiotemporal distribution by taking into account the binding of the mark to components of the test medium.

The object is also accomplished by providing the second variant of method for determining the spatiotemporal distribution of activity of a proteolytic enzyme in a heterogeneous system, comprising the steps of:

providing an in-vitro system that includes a sample of a test medium, wherein the test medium is selected from the group consisting of blood plasma, whole blood, water, lymph, colloidal solution, crystalloid solution and gel, and a proteolytic enzyme or its zymogen, wherein the proteolytic enzyme or its zymogen is distributed in the sample of the test medium;

combining (immersing or contacting) a chromogenous substrate with the in-vitro system, wherein the chromogenous substrate is cleaved by the proteolytic enzyme, and a chromogenic mark is released upon cleavage of the chromogenous substrate;

illuminating the sample of the test medium by light having a wavelength corresponding to substantial absorption thereof by the chromogenic mark;

recording the spatial distribution of light absorption of the chromogenic mark in the sample of the test medium, and obtaining a set of distributions of the light absorption points;

calculating the spatiotemporal distribution of the proteolytic enzyme activity by using the set of distributions of the light absorption and solving the inverse "reaction-diffusion-convection" problem, wherein the step of calculating includes correcting the spatiotemporal distribution by taking into account the binding of the mark to components of the test medium.

The object is also accomplished by providing the third variant of method for determining the spatiotemporal distribution of activity of a proteolytic enzyme in a heterogeneous system, comprising the following steps:

providing an in-vitro system that includes a sample of a test medium, wherein the test medium is selected from the group consisting of blood plasma, whole blood, water, lymph, colloidal solution, crystalloid solution and a gel, and a proteolytic enzyme or its zymogen, wherein the proteolytic enzyme or its zymogen is distributed in the sample of the test medium;

combining (immersing or contacting) a luminescent substrate with the in-vitro system, wherein the luminescent substrate is cleaved by the proteolytic enzyme and a luminescent mark is released upon cleavage of the luminescent substrate;

recording the spatial distribution of a luminescence signal of the luminescent mark in the sample, and obtaining a set of distributions of the luminescent signal;

calculating the spatiotemporal distribution of the proteolytic enzyme activity using the set of distributions of the luminescent signal and solving the inverse "reaction-diffusion-convection" problem;

wherein the step of calculating includes correcting the spatiotemporal distribution by taking into account the binding of the mark to components of the test medium.

It is also accomplished by further placing an activating agent into the in-vitro system to induce changes in spatiotemporal distribution of the proteolytic enzyme activity.

It is also accomplished by selecting an activating agent from the group consisting of tissue factor immobilized on a surface, soluble tissue factor, plasminogen tissue activator, a cell capable of expressing tissue factor, samples of body tissues, glass and plastic.

It is also accomplished by further including illuminating of the sample of the test medium and recording the spatial parameters of the test sample selected from the group consisting of the spatial distribution of light scattering, the spatial distribution of light transmission within the sample, or a combination thereof.

It is also accomplished by providing the method wherein the fluorogenic substrate, the chromogenous substrate, or the luminescent substrate is a solution.

It is also accomplished by providing the method wherein the fluorogenic substrate, the chromogenous substrate or the luminescent substrate is applied in the freeze-dried form, for example on the walls of the in-vitro system before placing the sample of the test medium.

It is also accomplished by providing the method wherein the test medium is blood plasma selected from the group consisting of platelet-rich plasma, platelet-free plasma, and platelet-poor plasma.

It is also accomplished by providing the method wherein the steps of illuminating or recording are performed with a frequency of 1 to 1800 times per minute.

It is also accomplished by providing the method wherein the step of recording is performed at a temperature of about 37 degrees C.

It is also accomplished by providing the method wherein the step of recording is performed at a constant pressure, where the constant pressure is a pressure elevated compared to the atmospheric pressure preferably elevated as to the atmospheric.

Preferably, pH of the sample of the test medium is stabilized within the range of 7.2-7.4.

The studied proteolytic enzyme in the test medium may come from the zymogen as a result of biochemical processes; it may also be gradually destroyed in the test medium as a result of biochemical processes within the system.

The spatial distributions of the mark and of the formed clot are visualized at given moments of time.

The light scattering from the test medium sample is registered using the dark-field microscopy.

The mark fluorescence is registered using the fluorescent microscopy method.

The registration of light scattering distribution and mark fluorescence distribution in the test medium is also executed using confocal microscopy providing refocusing of the optical system and of the illuminating/radiation processing systems at determined times.

The object is also accomplished by providing an apparatus for determining the spatiotemporal distribution of activity of a proteolytic enzyme in a heterogeneous system, comprising of:

an in-vitro system that includes a cuvette for placing a sample of a test medium, wherein the test medium is selected from the group consisting of blood plasma, whole blood, water, lymph, colloidal solution, crystalloid solution and gel, proteolytic enzyme or its zymogen, wherein the proteolytic enzyme or its zymogen is distributed in the sample of the test medium, and a substrate, wherein the substrate is selected from the group consisting of a fluorogenic substrate, a chromogenic substrate, and a luminescent substrate;

means to illuminate the sample of the test medium in determined times;

means to record the spatial distribution of a signal of a mark released upon cleavage of the abovementioned substrate by the proteolytic enzyme, means to control illuminating/recording means.

As well as while it is including means to place and insert into the cuvette the activator that induces changes of spatiotemporal distribution of proteolytic enzyme activity.

As well as while it is including means for providing a constant temperature within the sample of the test medium, preferably 37 degrees C.

As well as while it is including means for providing constant pressure within the volume of the sample of the test medium, preferably elevated compared to the atmospheric pressure.

As well as while it is including means of illuminating the sample of the test medium using dark-field microscopy.

As well as while it is including means to control illuminating means and recording means being capable of regulating time of switching on and off, an intensity of illumination and synchronization of the illuminating means and recording means.

As well as while it is including a computing device capable of calculating spatial distribution of proteolytic enzyme activity.

The object is further accomplished by providing a method for diagnosing disorders in the hemostatic system in a subject based on the change in the spatiotemporal distribution of activity of a proteolytic enzyme (coagulation factor) in a heterogeneous in-vitro system, comprising the steps of:

providing a test sample obtained from the subject that includes blood components selected from the group consisting of: whole blood, platelet-free blood plasma, platelet-poor blood plasma, platelet-rich blood plasma, blood with addition of anticoagulant, and blood plasma with addition of anticoagulant;

providing conditions for formation of a proteolytic enzyme in the test sample by performing at least one operation selected from the group consisting of: bringing the test sample into contact with the blood coagulation activator immobilized on a surface; adding a substrate to be cleaved by the proteolytic enzyme; adding a calcium salt; adding an inhibitor of the contact coagulation activation;

recording in determined moments of time the spatial distribution of the signal of a mark released upon cleavage of the substrate by the proteolytic enzyme, and obtaining a set of spatial distributions of the signal of the mark;

calculating (determining) the spatiotemporal distribution of the proteolytic enzyme activity by using the set of spatial distributions and solving the inverse "reaction-diffusion-convection" problem, wherein the proteolytic enzyme is a coagulation factor, wherein the step of calculating includes correcting the spatiotemporal distribution by taking into account the binding of the mark to components of the test medium.

assessing the state of hemostasis in the subject based on the spatiotemporal distribution of the proteolytic enzyme activity by comparing spatiotemporal distribution to a proper control.

As well as while it is further including illuminating the test sample and recording the spatial distribution of the light scattering resulted from the formed fibrin clot in the test sample by using dark-field microscopy.

As well as while it is including a coagulation factor being an enzyme selected from the group consisting of: thrombin, factor Xa, factor VIIa, factor IXa, factor XIIa, factor XIa, plasmin.

As well as while it is further including assessing the state of the coagulation system in the test sample using at least one parameter of the spatiotemporal distribution of thrombin or fibrin and making a diagnosis of a hemostatic system disorder in the subject, wherein the parameter is selected from the group consisting of: the rate of spatial propagation of the thrombin wave, the high concentration of thrombin in the sample, the high concentration of thrombin in the moving part of the wave, the rate of increase of thrombin concentration, the integral of thrombin concentration as function of space, the integral of thrombin concentration as function of time and space, the rate of spatial propagation of fibrin front, light scattering, and the high fibrin concentration in the test sample.

The proposed method allows modeling the in-vitro systems which are close in physiological properties to the in-vivo systems, as well as more accurately diagnosing disorders in the blood coagulation system.

The resulting spatiotemporal data array, i.e. the spatiotemporal distribution of the proteolytic enzyme activity, is used to compute at each point the rate of change of the proteolytic enzyme activity over space and time, according to which the following is possible:

judging on the state of the blood coagulation system in the sample;

making conclusion on the state of the coagulation system in a patient compared to healthy donors;

estimating efficiency of the therapy;

choosing an optimal individual dose of a medical preparation;

determining mechanism of action of the medical preparation;

screening chemical substances in course of development of medical preparations;

acquiring information about the operation mechanism of the blood coagulation system;

studying pathogenesis and etiology of blood system disorders;

studying spatial dynamics of coagulation factors in the process of fibrin clot growth;

enabling assessment of the role of coagulation factor in different blood coagulation phases in a heterogeneous system.

The present method ensures a reliable diagnosis of hypercoagulation states at early stages, when all other tests cannot reveal them. For the first time in medical practice, this allows detecting with a high degree of accuracy the predisposition of patients to a wide range of pathologies, including hypercoagulation syndromes of various etiology, hemorrhages, thromboses, heart attacks, and strokes; studying pathogenesis of diseases; monitoring traditional and new generation medicines, including anti-hemophilia preparations.

The present apparatus allows implementing the inventive method and ensuring a more accurate determination of the spatiotemporal distribution of activity of a proteolytic enzyme in a heterogeneous system.

BRIEF DESCRIPTION OF DRAWINGS

The invention will be further illustrated by description of preferred embodiments thereof with reference to the accompanying drawings, where:

FIG. 5a-b shows visualization of spatial dynamics of formation of a fibrin clot (a) and a fluorophore (b), according to the invention;

FIG. 6a-b depict an example of spatiotemporal dynamics of formation of a fibrin clot (a) and concentration of proteolytic enzyme (thrombin) (b) in an in-vitro system, obtained using the apparatus according to the invention; the clotting activator is at the origin of coordinates.

DESCRIPTION OF EMBODIMENTS

First Embodiment of the Method

According to the invention, a method provided for determining the spatiotemporal distribution of activity of a proteolytic enzyme in a heterogeneous system is implemented as follows.

An in-vitro system that includes a sample of a test medium, wherein the test medium is selected from the group consisting of blood plasma, whole blood, water, lymph, colloidal solution, crystalloid solution and gel, and a proteolytic enzyme or its zymogen, wherein the proteolytic enzyme or its zymogen is distributed in the sample of the test medium.

A fluorogenic substrate is combined (or immersed, or contacted) with the in-vitro system.

In reaction between the proteolytic enzyme and the fluorogenic substrate, the fluorogenic substrate is cleaved by the proteolytic enzyme, and a fluorescent mark (fluorophore) is released upon cleavage of the fluorogenic substrate.

The sample of the test medium is illuminated with exciting radiation (in determined times) to excite a fluorescence signal of the fluorescent mark; simultaneously (in determined times), the spatial distribution of the fluorescence signal of the fluorescent mark in the sample of the test medium is recorded.

In addition to recording of the spatial distribution of the mark in the sample, it is possible to illuminate the test medium sample in determined times and to record optical characteristics of the sample selected from the group consisting of: the spatial distribution of light scattering, the spatial distribution of light transmission in the sample, or a combination thereof. Therewith, the spatial distribution of fibrin is recorded.

The spatiotemporal distribution of the proteolytic enzyme activity is calculated by using the set of spatial distributions of the fluorescence signal and solving the inverse "reaction-diffusion-convection" problem. The step of calculating includes correcting the spatiotemporal distribution by taking into account the binding of the mark to components of the test medium.

The excitation wavelength is selected in accordance with the excitation spectrum of the mark (fluorophore). The illumination wavelength is selected so as to ensure a maximum signal/noise ratio; in particular, within the coagulation system study, signal is the light scattering from the fibrin clot, and noise is the light scattering from plasma and other elements of the in-vitro system.

In the experiments, an activating agent can be added in the in-vitro system to induce a change in the spatiotemporal distribution of the proteolytic enzyme activity. The activating agent can be an agent selected from the group consisting of: tissue factor immobilized on the surface, soluble tissue factor, tissue-type plasminogen activator, cells with ability of tissue factor expression, samples of body tissues, glass or plastic.

In the embodiment, the proteolytic enzyme under analysis is formed directly in the test medium from its zymogen, as a result of biochemical processes. In another embodiment, the analyzed proteolytic enzyme is gradually destroyed in the test medium due to biochemical processes occurring in the medium.

Spatial distributions of light scattering and fluorescence of the mark in the sample can be recorded by means of confocal microscopy, which provides refocusing of the optical system and the illuminating/radiation processing system in determined times, or by means of fluorescence microscopy.

Spatial distribution of the mark and the resulting clot are further visualized in determined times.

Light scattering from the test medium sample is recorded using the dark-field microscopy.

Second Embodiment of the Method

The second embodiment differs from the first embodiment in that the substrate is a chromogenic substrate.

In reaction between the proteolytic enzyme and the chromogenic substrate, the substrate is cleaved and releases a chromophore. The system is illuminated with light having a wavelength at which the light is substantially absorbed by the chromophore. Spatial distribution of the change of color of the test medium is recorded in determined times. Spatial distribution of the chromophore in the sample is determined from the spatial distribution of the change of color of the sample. Spatiotemporal distribution of the proteolytic enzyme activity is calculated by using the set of spatial distributions of the chromophore and solving the inverse "reaction-diffusion-convection" problem. The step of calculating includes correcting the spatiotemporal distribution by taking into account the binding of the mark to components of the test medium.

In determined times, the sample of the test medium is illuminated, and optical characteristics of the sample selected from the group consisting of: the spatial distribution of light scattering, the spatial distribution of optical transmission in the sample, or a combination thereof, are recorded by the photographic camera.

Third Embodiment of the Method

The third embodiment of the method is different from the first embodiment in that the substrate is a substrate which is cleaved in reaction with the proteolytic enzyme to release a chemiluminescent product. Spatial distribution of luminescence intensity in the sample is recorded in determined times. Spatiotemporal distribution of activity of the proteolytic enzyme is calculated by using the set of spatial distributions of the luminescence and solving the inverse "reaction-diffusion-convection" problem. The step of calculating includes correcting the spatiotemporal distribution by taking into account the binding of the mark to components of the test medium.

In determined times, the test medium sample is illuminated, and optical characteristics of the test sample, selected from the group consisting of: the spatial distribution of light scattering, the spatial distribution of optical transmission in the sample, or a combination thereof are recorded by the photographic camera.

In all embodiments of the method, the constant temperature is maintained in the whole volume of the in-vitro system, preferably of about 37 degrees C.; the system is thermally regulated for this purpose. To avoid formation of air bubbles in the test sample, the pressure in the in-vitro system is maintained preferably at an elevated level as to the atmospheric one. The pH of the sample is stabilized to the range of 7.2-7.4.

The substrate can be added to the sample of the test medium in the form of a solution. It is also possible to apply the substrate in the freeze-dried form, for example on the walls of the in-vitro system before placing the sample of the test medium.

Illuminating and recording of the mark signal are performed with a frequency of 1 to 1800 times per minute. Illumination is carried out after establishing a constant temperature in the sample.

A mixture is prepared out of test plasma sample, contact phase inhibitor, calcium chloride, and substrate specific to the tested coagulation factor; this mixture is used for all variations of the study.

The sample is, in particular, whole blood or plasma selected from the group consisting of: platelet-rich plasma, platelet-free plasma, and platelet-poor plasma.

The analyzed coagulation factor is, in particular, thrombin.

According to the invention, a method is also provided for diagnosing disorders in the hemostatic system based on the change of the spatiotemporal distribution of activity of a proteolytic enzyme (coagulation factor) in a heterogeneous in-vitro system: the method involves the use as a sample of blood components selected from the group consisting of: whole blood, platelet-free plasma, platelet-poor plasma, platelet-rich plasma, blood with addition of anticoagulant, blood plasma with addition of anticoagulant.

Conditions are provided for formation of a proteolytic enzyme in the test sample and for observation thereof by performing at least one operation selected from the group consisting of: bringing the test sample into contact with the blood coagulation activator immobilized on a surface; adding a substrate to be cleaved by the studied proteolytic enzyme; adding a calcium salt; adding an inhibitor of the contact coagulation activation.

In determined times, the spatial distribution of the signal of the mark within the sample cleaved from the substrate is recorded.

The temperature of the sample is maintained constant with the accuracy of 1 degree in the range of 25-45 degrees C. pH of the sample is stabilized in the range of 7.2-7.4.

Spatiotemporal distribution of the proteolytic enzyme activity (coagulation factor) is calculated by using the set of spatial distributions of the mark signal and solving the inverse "reaction-diffusion-convection" problem. At the basis thereof, the spatiotemporal distribution of the coagulation factor distribution in time is calculated. The step of calculating includes correcting the spatiotemporal distribution by taking into account the binding of the mark to components of the test medium.

The state of hemostasis in the subject is assessed basing on the spatiotemporal distribution of the proteolytic enzyme activity by comparing spatiotemporal distribution to a proper control.

Additionally, the test sample is illuminated in determined times, and spatial distribution of the light scattering from the formed fibrin clot in the test medium sample is recorded to visualize the formed fibrin clot.

The investigated coagulation factor is the proteolytic enzyme selected from the group: thrombin, factor Xa, factor VIIa, factor IXa, factor XIIa, factor XIa, plasmin.

At least one parameter of spatiotemporal thrombin or fibrin distribution is used in order to assess the state of the coagulation system in the sample and to make a diagnosis; the parameter is selected from the group consisting of: the rate of spatial propagation of the thrombin wave, the high concentration of thrombin in the sample, the high concentration of thrombin in the moving part of the wave, the rate of increase of thrombin concentration, integral of thrombin concentration according to space, the integral of thrombin concentration as function of time and space, the rate of spatial propagation of fibrin front, light scattering and the high fibrin concentration (volume of light scattering) in the test sample.

The device (apparatus) for realization of the said method (the variations of execution thereof) determining the spatiotemporal distribution of activity of a proteolytic enzyme in a heterogeneous system comprises an in-vitro system that includes cuvette 20 (FIG. 4) to place sample 21 of a test medium selected from the group consisting of: blood plasma, whole blood, water, gel and lymph, colloidal solution, crystalloid solution and gel, and a proteolytic enzyme or its zymogen, wherein the proteolytic enzyme or its zymogen is distributed in the sample of the test medium. The cuvette 20 has specific geometric dimensions and form, rectangular cross-section, and is made of plastic.

To reduce convective flows (the thinner the layer, the faster the liquid motion decays) and to ensure fast heating, the thickness of the sample layer should be minimal. To increase the signal strength, the sample layer thickness should be maximal. The optimum thickness is between 0.1-1.5 mm.

Figure 4:
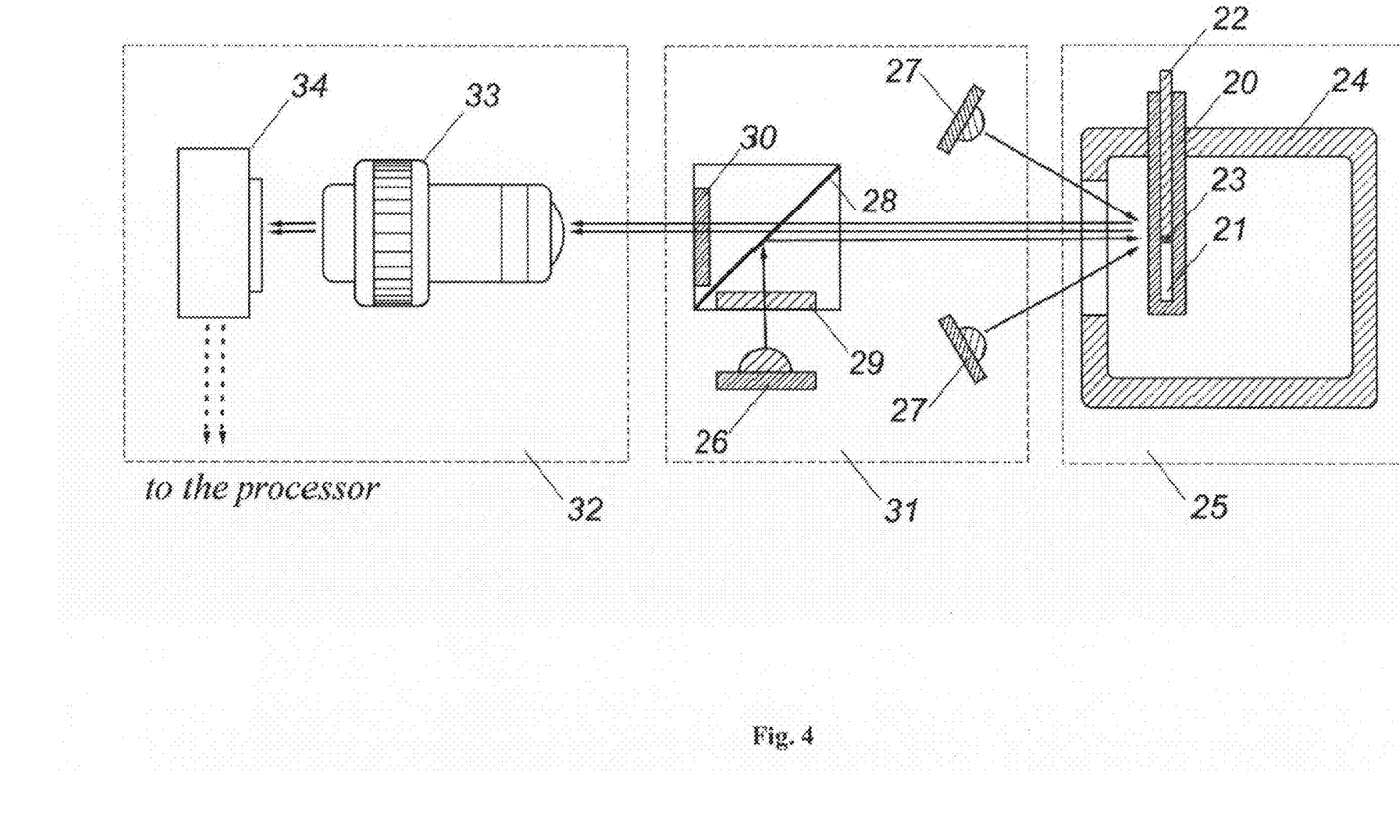
FIG. 4 is a schematic diagram of an apparatus for determining the spatiotemporal distribution of activity of a proteolytic enzyme in a heterogeneous system, according to the invention.

The apparatus further includes activating means 22 designed to place and insert into the cuvette a process activator 23 that induces a change of the spatiotemporal distribution of proteolytic enzyme activity.

The device (apparatus) further includes means 24 for ensuring a constant temperature in the in-vitro system. The device enables different types of temperature control, including water temperature control and air temperature control; gel can also be used for temperature control, but in this case it should be taken into account that the medium must be transparent to the radiation. In the described embodiment, water temperature control is used. For temperature control, the temperature is maintained within the range of 25-45 degrees C. with the accuracy of one degree C. The apparatus also includes means (not shown) for maintaining pressure in the in-vitro system; said means are designed to maintain a constant air pressure in the space surrounding the test sample medium (together with means 24 for maintaining a constant temperature they form temperature and pressure control unit 25). The means maintain an excess pressure from 0.2 to 0.5 atm, which prevents formation of gas bubbles in the sample under analysis. Formation of bubbles is due to the decrease of solubility of dissolved gases contained in the sample. Usually, this phenomenon is associated with heating of the sample. Bubbles give rise to local distortions, both in terms of making the medium less physiological, i.e. drift from the simulated conditions, and in terms of calculating the distribution of enzymes.

The apparatus includes means 26 for illuminating sample 21 of the test medium in determined times with exciting radiation to excite fluorescence of the mark in case of addition to the sample of fluorogenic substrate, or with the light with a wavelength corresponding to substantial absorption thereof by the mark in case of addition of chromogenic substrate to the sample. Means 26 apply radiation perpendicularly to the wall of cuvette 20 through a window in thermostat 24. Illuminating means 26 comprises UV sources, for example, UV LEDs. Means 27 for illuminating the test medium sample with visible light provides light at an angle to the wall of cuvette 20. The apparatus contains mirror 28 for directing the radiation to the cuvette, as well as excitation filter 29 and emission filter 30 for extracting the fluorescence signal. The emission of the optical elements should not cause local heating of the sample. The combination of means 26-30 forms illuminating/lightening unit 31.

The apparatus further includes unit 32 for recording the spatial distribution of the mark fluorescence intensity/light scattering (or absorption by the chromophore mark) in the sample of the test medium in determined times. The recording unit 32 includes means for taking images from different depths of the sample, including optical system 33 for focusing the optics, and apertures (not shown). The fluorescence intensity depends on the activity of the proteolytic enzyme under analysis. Fluorescence from the substrate propagates perpendicularly to the wall of cuvette 20, passes through mirror 28 being transparent to this emission spectrum, then through emission filter 30 and enters through optical system 33 into recording device 34 which can be represented by a digital photographic camera.

The apparatus includes means to control illuminating/lightening means such as a processor (not shown) and the recording means (not shown) are capable of regulating time of switching on and off, an in an intensity and duration of illuminating/lightening and synchronization of operation of the illuminating/lightening means and the recording means.

A computing device (not shown) calculates the spatial distribution of the proteolytic enzyme activity over time.

Means for visualizing the forming/dissolving clot by the dark-field microscopy and means for visualizing the spatial image of formation/destruction of mark (fluorophore/chromophore) (not shown) are also connected to the control means.

The functioning of the apparatus and the way of definition of the spatiotemporal distribution of the proteolytic enzyme activity in the heterogeneous system is considered hereinafter as an inexhaustive example of execution.

Materials

The following agents were used: phosphatidylserine and phosphatidylcholine; 7-amino-4-methyl-coumarin (AMC); Z-Gly-Gly-Arg-AMC; corn trypsin inhibitor; factor VIII; factor VIII test; factor VIII-deficient plasma; glycoprotein IIb-IIIa antagonist.

Blood Collection and Plasma Preparation

Samples of normal plasma were obtained from fresh human blood of healthy donors. Blood was collected in 3.8% sodium citrate (pH 5.5) at the ratio of 9:1 by volume. Blood was centrifuged for 15 min at 1600 g, and the supernatant was then further centrifuged for 5 min at 10 000 g to obtain platelet-free plasma; the supernatant was then frozen and stored at −70 degrees C. Before each experiment, samples were thawed in a water bath.

To prepare platelet-rich plasma, blood was centrifuged at 100 g for 8 minutes. The concentration of platelets was brought to 250 000 cells/µl by dissolving with a platelet-free plasma. To stabilize pH, 28 mM of Hepes were added into plasma (pH 7.4).

Commercially available plasmas deficient in some clotting factors were thawed and treated with Hepes to stabilize pH, as was done with platelet-rich plasma.

Preparation of the Activator

As mentioned earlier, coagulation was activated using an activator—a monolayer of tissue factor (TF) immobilized on a plastic surface. Activators were stored at +4 to +8 degrees C.

Experiment

Spatial clot growth in different test medium samples was considered.

A) Spatial Clot Growth in Platelet-Free Plasma

The plasma prepared as stated above was supplemented with an inhibitor, for example, corn tripsin inhibitor (0.2 mg/ml), 0.1 µM lipid vesicles (phosphatidylserine/phosphatidylcholine in 20/80 molar ratio). A substrate Z-GGR-AMC (800 µM) was added for monitoring the formation of thrombin. The sample was incubated for 10 min at 37 degrees C., then a calcium salt was added, in particular, $CaCl_2$ (20 mM). The investigated sample was put into the experimental cuvette, and the formation of clot was initiated by the activator, the surface of which was covered with tissue factor: the activator was brought into contact with the prepared plasma sample.

Figure 5:
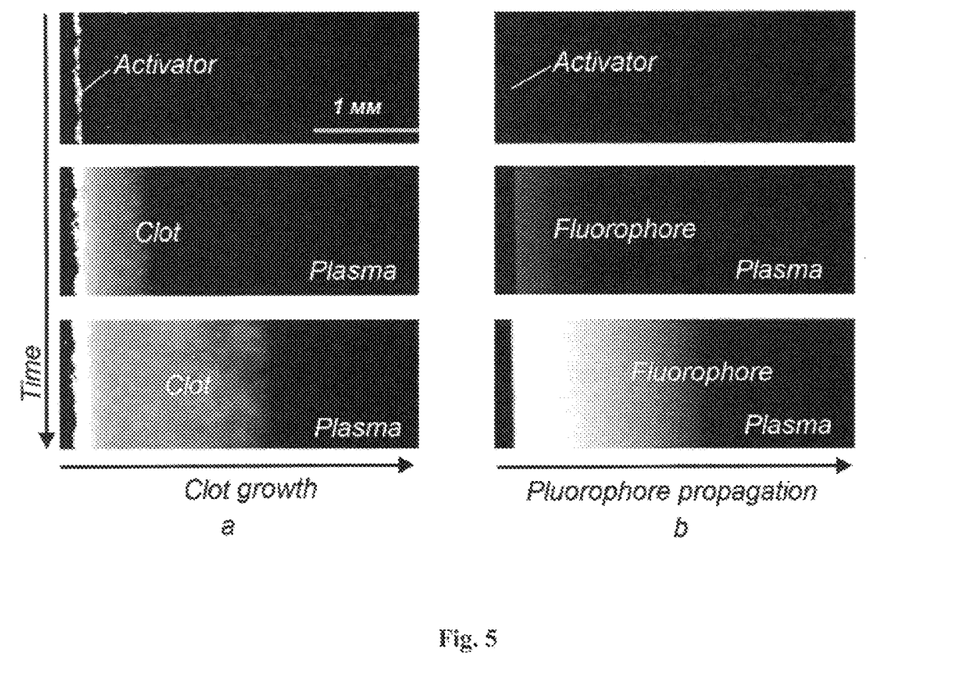

Experiments were performed using specially designed video microscopy system which allowed simultaneous observing of the spatial distribution or growth of fibrin clot and proteolytic enzyme, in particular, thrombin. The temperature in the chamber was maintained at 37 degrees C., and illumination was performed by red (625 nm) and ultraviolet (365 nm) LEDs. Growth of the clot was detected from light scattering of the sample when illuminated with red light (FIG. 5a), and AMC fluorescence was excited by ultraviolet LEDs (FIG. 5b). A multilane emissive filter was used to isolate the red light scattering, AMC emission, and exciting emission. Fluorescence and scattering of the red light passing through a macro lens were detected by a digital CCD camera. Images in red and blue light were obtained sequentially, usually one to four times per minute. To prevent AMC burnout, LEDs were synchronized with the camera and switched on only for the duration of exposure, i.e. for about 0.5 sec.

B) Spatial Clot Growth in Platelet-Rich Plasma

To prevent retraction of the clot, 25 µg/ml of glycoprotein inhibitor IIb/IIIa was used. Also, experiments were performed on 0.5% low melting temperature agarose gel, because in some cases even a high concentration of antagonist didn't completely inhibit the retraction.

Samples were prepared as described above, except for using platelet-rich plasma instead of platelet-free plasma. After recalcification, plasma was preheated to 42 degrees C. for 2 minutes. Agarose solution was added, and the mixture was incubated in an experimental chamber for 3 min to form a gel. Then the experiment was initiated as described above.

Data Processing

Image Processing

Figure 6:
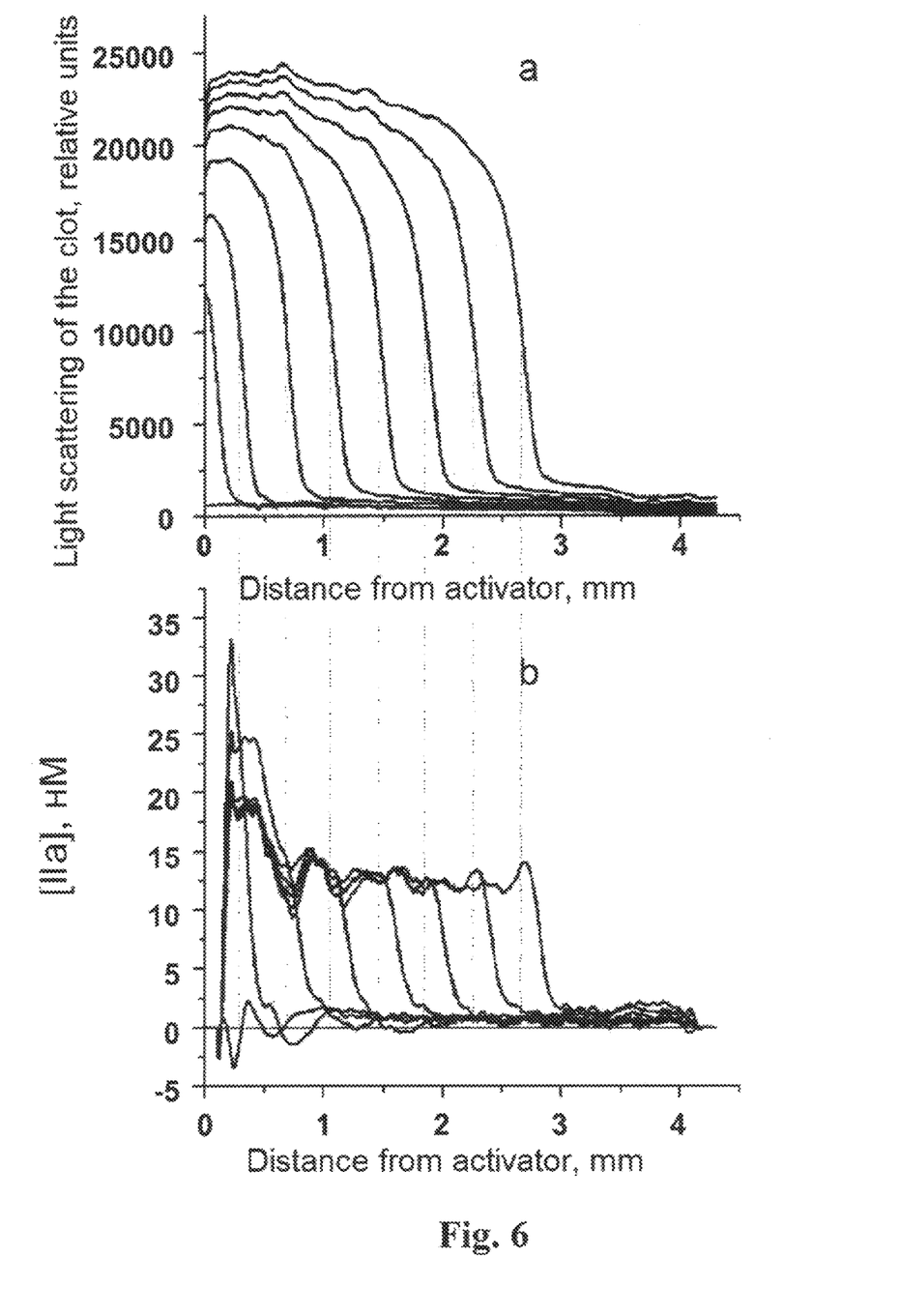

Images in red and ultraviolet light were initially processed in the same way. To obtain profiles of light scattering (FIG. 6a) or AMC fluorescence, the light intensity was measured for each frame in the respective range along the line perpendicular to the surface of the activator. The values were averaged to 150-300 lines.

The clot growth rate was calculated from the movement of a half-maximal intensity point on light scattering profiles. The initial growth rate was determined as the slope of the linearized portion of the clot size time dependence diagram in the first 10 min of its growth. The steady rate was calculated in the same way, after 40 min of growth of the clot; when the clot boundary is so far from the activator, the effect thereof on the growth of the clot becomes insignificant.

Profiles of AMC fluorescence intensity were converted into profiles of its concentration by means of calibration. The intensity calibration profile was calculated within the uniform distribution with a known AMC concentration in the same plasma. AMC concentration at each point ($C_i$) was calculated as follows:

$$C_i = \frac{(I_i - I_{bgr}) * C_{cal}}{(I_{cal} - I_{bgr})}$$

where: $I_i$ is fluorescence intensity, $I_{bgr}$ is background intensity, $I_{cal}$ is fluorescence intensity with a known AMC concentration, all at the same point of the frame, and $C_{cal}$ is calibration concentration of AMC.

Calculation of Thrombin Concentration

Concentration of thrombin (FIG. 6b) was calculated from one-dimensional distribution of AMC by solving the inverse problem for the following reaction-diffusion equation:

$$\frac{\partial AMC}{\partial t} D_{AMC} \frac{\partial^2 AMC}{\partial x^2} + k_{cat} \frac{IIa \times S}{K_m + S}$$

$$IIa(x,t) = \frac{K_m + S}{S \times k_{cat}} \left( \frac{\partial AMC(x,t)}{\partial t} - D_{AMC} \frac{\partial^2 AMC(x,t)}{\partial x^2} \right)$$

where: AMC, S and IIa are concentrations of AMC, fluorogenic substrate and thrombin, respectively; $D_{AMC}$ is AMC diffusion coefficient; $K_m$, $k_{cat}$ are Michaelis constants, or constants of reaction of the substrate cleavage by thrombin.

The AMC diffusion coefficient was measured experimentally by fitting the experimental diffusion profiles to the theoretical ones.

The inverse problem for distribution of thrombin concentration is ill-conditioned, so the experimental noise and even small AMC profile distortions lead to the absence of solution thereof. To overcome this, numerical algorithms were used to reduce noise and distortion levels of the AMC signal.

AMC signal distortions are due to excitation of light scattering on the fibrin clot. Intensity of fluorescence increases inside the clot. This increase is proportional to the AMC concentration and the clot density. To overcome this and to calculate the actual AMC concentration, the following formula was used:

$$AMC_{visible} = AMC_{real} + (k_1 + k_2 \cdot AMC_{real}) \frac{Clot}{k_2}$$

where: $AMC_{visible}$ is AMC concentration obtained by calibration; $AMC_{real}$ is real AMC concentration; Clot is scattering of light intensity by fibrin; coefficients $k_1$, $k_2$, $k_3$ have been measured experimentally.

To reduce noise, the following algorithms of calculation of derivatives were used:

$$\frac{\partial [AMC]}{\partial t} = \frac{1}{J} \sum_j^J \frac{[AMC](x, t + j * \Delta t) - [AMC](x,t)}{j * \Delta t}$$

-continued $$\frac{\partial^2 [AMC]}{\partial x^2} =$$

$$\frac{1}{I}\sum_i^I \frac{[AMC](x+i*\Delta x, t) - 2\cdot[AMC](x,t) + [AMC](x-i*\Delta x, t)}{(i*\Delta x)^2}$$

where: $\Delta t$ is time between frames, typically 1 min; $\Delta x$ is pixel size (4.3 μm); values of I and J are chosen optimal so as to minimize noise at minimal distortion of the signal. Typically, J=3 and I=40 were selected, in this case summing could start from I and J values greater than unity.

The invention claimed is:

1. A method for determining the spatial distribution of activity of a proteolytic coagulation factor in the determined points of time in vitro comprising the steps of:
obtaining a sample of a test medium from the subject, wherein the test medium is one of blood plasma and whole blood;
adding a fluorogenic substrate to the test medium to obtain a test medium with the fluorogenic substrate;
combining the test medium with the fluorogenic substrate and an activating agent in a cuvette of an in vitro system, wherein the activating agent induces the formation of an activated proteolytic coagulation factor from its inactive zymogen and causes the formation of a fibrin clot, the fluorogenic substrate is cleaved by the activated proteolytic coagulation factor, and a fluorescent mark is released upon cleavage of the fluorogenic substrate and the activating agent is a tissue factor;
providing and maintaining constant pressure within the in vitro system, wherein the constant pressure is a pressure elevated compared to the atmospheric pressure;
illuminating the cuvette with the light of the fluorescent mark's excitation wavelength in determined points of time to excite a fluorescence signal of the fluorescent mark;
recording the spatial distribution of the intensity of the fluorescence signal within a volume of the cuvette in the determined points of time, and obtaining a set of recorded spatial distributions of the intensity of the fluorescence signal;
illuminating the cuvette with the light of visible wavelength in determined points of time to induce light scattering by the fibrin clot;
recording the spatial distribution of the intensity of the light scattering signal within a volume of the cuvette in the determined points of time, and obtaining a set of recorded spatial distributions of the intensity of the light scattering signal;
converting the set of the recorded spatial distributions of the intensity of the fluorescence signal into a set of spatial distributions of the activity of the proteolytic coagulation factor in the determined points of time by solving the inverse "reaction-diffusion-convection" equation, wherein the step of converting further includes correction of the distortion of the fluorescence signal caused by light scattering in the fibrin clot at each of the determined points of time wherein the set of spatial distributions of the activity of the proteolytic coagulation factor in the determined point of time reflects the state of coagulation system of the subject.

2. A method for determining the spatial distribution of activity of a proteolytic coagulation factor in the determined points of time in vitro comprising the steps of:
obtaining a sample of a test medium from the subject, wherein the test medium is one of blood plasma and whole blood;
adding a chromogenous substrate to the test medium to obtain a test medium with the chromogenous substrate;
combining the test medium with the chromogenous substrate and an activating agent in a cuvette of an in-vitro system, wherein the activating agent induces the formation of an activated proteolytic coagulation factor from its inactive zymogen and causes the formation of a clot, the chromogenous substrate is cleaved by the activated proteolytic coagulation factor, and a chromogenic mark is released upon cleavage of the chromogenous substrate and the activating agent is a tissue factor;
providing and maintaining constant pressure within the in vitro system, wherein the constant pressure is a pressure elevated compared to the atmospheric pressure;
illuminating the cuvette by light having a wavelength corresponding to substantial absorption thereof by the chromogenic mark in determined points of time;
recording the spatial distribution of light absorption of the chromogenic mark within a volume of the cuvette in determined points of time and obtaining a set of recorded spatial distributions of the light absorption points;
illuminating the cuvette with the light of visible wavelength in determined points of time to induce light scattering by the fibrin clot;
recording the spatial distribution of the intensity of the light scattering signal within a volume of the cuvette in the determined points of time, and obtaining a set of recorded spatial distributions of the intensity of the light scattering signal;
converting the set of the recorded spatial distributions of the light absorption of the chromogenic mark into a set of spatial distributions of the activity of the proteolytic coagulation factor in the determined points of time by solving the inverse "reaction-diffusion-convection-"equation, wherein the step of converting further includes correction of the distortion of the light absorption caused by light scattering in the fibrin clot at each of the determined points of time, wherein the set of spatial distributions of the activity of the proteolytic coagulation factor in the determined points of time reflects the state of coagulation system of the subject.

3. A method for determining the spatial distribution of activity of a proteolytic coagulation factor in the determined points of time in vitro comprising the steps of:
obtaining a sample of a test medium from the subject, wherein the test medium is one of blood plasma and whole blood;
adding a luminescent substrate to the test medium to obtain a test medium with the luminescent substrate;
combining the test medium with the luminescent substrate and an activating agent in a cuvette of an in-vitro system, wherein the activating agent induces the formation of an activated proteolytic coagulation factor from its inactive zymogen and causes the formation of a clot, the luminescent substrate is cleaved by the activated proteolytic coagulation factor, and a luminescent mark is released upon cleavage of the luminescent substrate and the activating agent is a tissue factor;
providing and maintaining constant pressure within the in vitro system, wherein the constant pressure is a pressure elevated compared to the atmospheric pressure;

recording the spatial distribution of the intensity of a luminescence signal of the luminescent mark within a volume of the cuvette in the determined points of time, and obtaining a set of recorded spatial distributions of the intensity of the luminescent signal;

illuminating the cuvette with the light of visible wavelength in determined points of time to induce light scattering by the fibrin clot;

recording the spatial distribution of the intensity of the light scattering signal within a volume of the cuvette in the determined points of time, and obtaining a set of recorded spatial distributions of the intensity of the light scattering signal;

converting the set of the recorded spatial distributions of the intensity of the luminescent signal into a set of spatial distributions of the activity of the proteolytic coagulation factor in the determined points of time by solving the inverse "reaction-diffusion-convection-"equation, wherein the step of converting further includes correction of the distortion of the light absorption caused by light scattering in the fibrin clot at each of the determined points of time, wherein the set of spatial distributions of the activity of the proteolytic coagulation factor in the determined points of time reflects the state of coagulation system of the subject.

4. The method according to any one of claims 1 to 3, wherein the tissue factor is selected from the group consisting of tissue factor immobilized on a surface, and soluble tissue factor.

5. The method according to any one of claims 1 to 3, wherein the fluorogenic substrate, the chromogenous substrate, or the luminescent substrate is a solution.

6. The method according to any one of claims 1 to 3, wherein the fluorogenic substrate, the chromogenous substrate, or the luminescent substrate is applied in the freeze-dried form.

7. The method according to any one of claims claims 1 to 3, wherein the blood plasma is selected from the group consisting of platelet-rich plasma, platelet-free plasma, and platelet-poor plasma.

8. The method according to any one of claims 1 to 3, wherein the steps of illuminating or recording are performed with a frequency of 1 to 1800 times per minute.

9. The method according to any one of claims 1 to 3, wherein the in vitro system is maintained at a temperature of about 37 degrees C.

10. The method according to any one of the claims 1 to 3, wherein a pH of the test medium is stabilized within the range of 7.2-7.4.

11. The method according to any one of claims 1 to 3 further comprising visualizing the set of the recorded spatial distributions of the intensity of the fluorescence signal, light absorption of the chromogenic mark, or the intensity of the luminescent signal and the set of the recorded spatial distributions of the intensity of the light scattering signal.

12. The method according to any one of claims 1 to 3, wherein the correction includes subtracting a second value from a first value, wherein the first value is a value of the recorded intensity of the fluorescence signal in each point within the volume of the cuvette and the second value is the first value multiplied by a coefficient proportional to the recorded intensity of the light scattering signal in the corresponding point within the volume of the cuvette.

13. The method according to any one of claims 1 to 3 further comprising determining at least one parameter of a coagulation system by using the set of spatial distributions of the activity of the proteolytic coagulation factor and the set of the recorded spatial distributions of intensity of the light scattering signal, wherein the at least one parameter is selected from the group consisting of: the rate of spatial propagation of the proteolytic coagulation factor wave from the activating agent, the peak activity of the proteolytic coagulation factor, the peak activity of the proteolytic coagulation factor in the moving part of the wave, the rate of spatial propagation of the fibrin front from the activating agent, the rate of increase of the proteolytic coagulation factor activity, the integral of the proteolytic coagulation factor activity as function of space, the integral of the proteolytic coagulation factor activity as function of time and space, and the peak fibrin concentration in the test medium.

* * * * *